United States Patent
Heller

(10) Patent No.: US 12,350,514 B1
(45) Date of Patent: Jul. 8, 2025

(54) LASER DEVICES GENERATING TIME STRUCTURED LASER PULSES FOR SELECTIVE TARGETING OF TISSUES AND USES THEREOF

(71) Applicant: Light Age, Inc., Somerset, NJ (US)

(72) Inventor: Donald F. Heller, Somerset, NJ (US)

(73) Assignee: Light Age, Inc., Somerset, NJ (US)

( * ) Notice: Subject to any disclaimer, the term of this patent is extended or adjusted under 35 U.S.C. 154(b) by 0 days.

(21) Appl. No.: 16/270,357

(22) Filed: Feb. 7, 2019

Related U.S. Application Data

(63) Continuation of application No. 14/994,814, filed on Jan. 13, 2016, now abandoned, which is a continuation of application No. 13/831,369, filed on Mar. 14, 2013, now abandoned.

(51) Int. Cl.
*A61N 5/06* (2006.01)
*A61N 5/067* (2006.01)

(52) U.S. Cl.
CPC ......... *A61N 5/0624* (2013.01); *A61N 5/0613* (2013.01); *A61N 5/0616* (2013.01); *A61N 5/067* (2021.08)

(58) Field of Classification Search
CPC ............... A61N 5/0624; A61N 5/0616; A61N 2005/067; A61N 5/067; A61N 5/0613
See application file for complete search history.

(56) References Cited

U.S. PATENT DOCUMENTS

| | | | | |
|---|---|---|---|---|
| 6,090,788 A | * | 7/2000 | Lurie | A61P 43/00 514/23 |
| 7,033,381 B1 | * | 4/2006 | Larsen | A61N 5/0616 607/90 |
| 7,914,523 B2 | * | 3/2011 | Barolet | A61N 5/062 606/9 |
| 2005/0049657 A1 | * | 3/2005 | Jay | A61B 18/18 607/88 |
| 2006/0212025 A1 | * | 9/2006 | McDaniel | A61N 5/0617 606/9 |
| 2006/0212098 A1 | * | 9/2006 | Demetriou | A61N 5/0616 424/61 |
| 2007/0244526 A1 | * | 10/2007 | Zaghetto | A61N 5/0616 607/89 |
| 2008/0267814 A1 | * | 10/2008 | Bornstein | A61N 5/06 422/22 |
| 2010/0049180 A1 | * | 2/2010 | Wells | A61N 5/0616 606/11 |

(Continued)

FOREIGN PATENT DOCUMENTS

WO   WO-2011011644 A2 * 1/2011 ........... A61N 5/0616

Primary Examiner — Pamela M. Bays
(74) Attorney, Agent, or Firm — GREENBERG TRAURIG, LLP

(57) ABSTRACT

In some embodiments, the instant invention includes a laser device that includes: a laser generating module that produces a plurality of laser pulses having a time-stricture pulse format that includes at least: a plurality of micropulses, a macropulse time envelope, where the plurality of micropulses are within the macropulse time envelope; where the time-stricture pulse format is configured so that the laser device is capable of treating human tissue by selectively targeting or affecting at least one first tissue or at least one first disease organisms while not substantially affecting at least one first surrounding or adjacent tissue.

8 Claims, 3 Drawing Sheets

(56) References Cited

U.S. PATENT DOCUMENTS

| | | | |
|---|---|---|---|
| 2010/0234925 A1* | 9/2010 | Harris | A61N 5/0616 607/88 |
| 2011/0306955 A1* | 12/2011 | Thorhauge | A61B 18/203 606/9 |
| 2012/0010684 A1* | 1/2012 | Owens | A61N 5/0616 607/88 |

* cited by examiner

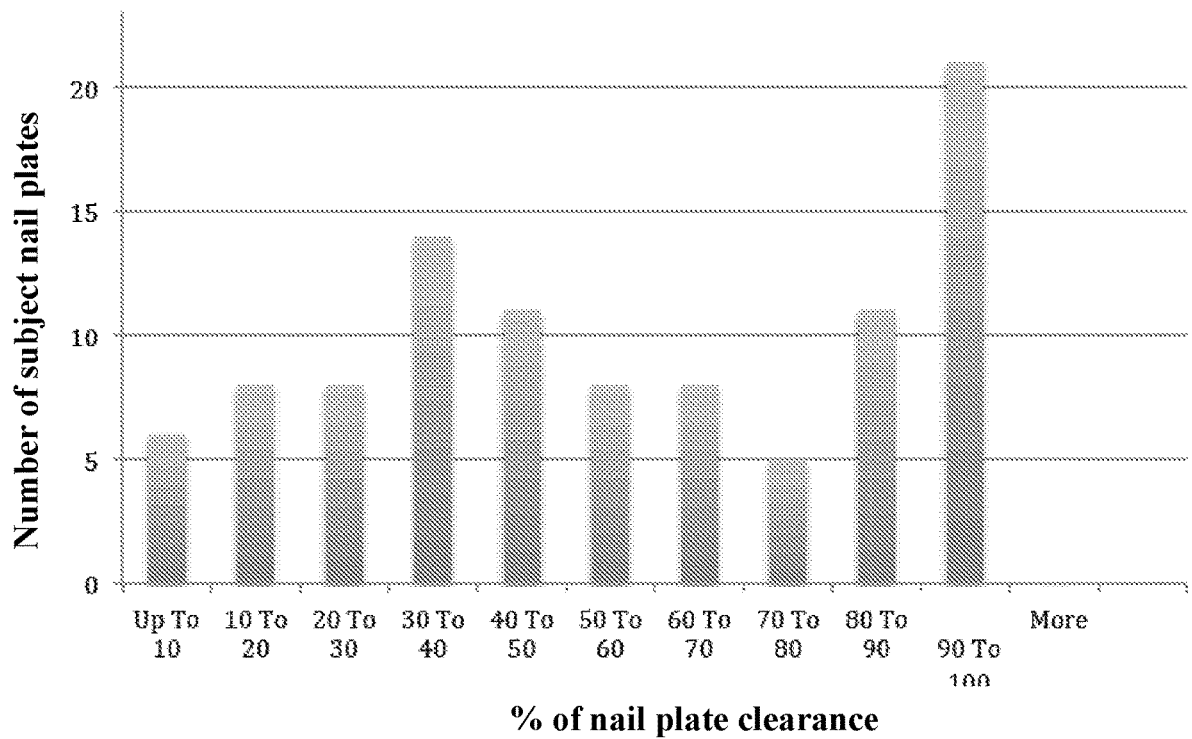
FIG. 3: Results of Clinical Study of nail plate clearance post laser treatment (N=100)

LASER DEVICES GENERATING TIME STRUCTURED LASER PULSES FOR SELECTIVE TARGETING OF TISSUES AND USES THEREOF

RELATED APPLICATIONS

This application is a continuation of U.S. patent application Ser. No. 14/994,814 filed on Jan. 13, 2016 which is a continuation of U.S. patent application Ser. No. 13/831,369, filed Mar. 14, 2013, entitled "LASER DEVICES GENERATING TIME STRUCTURED LASER PULSES FOR SELECTIVE TARGETING OF TISSUES AND USES THEREOF", which is incorporated herein by reference in its entirety for all purposes.

TECHNICAL FIELD

In some embodiments, the instant invention relates to laser systems that utilize time structured laser pulses selective targeting of tissue.

BACKGROUND OF THE INVENTION

Typically, laser devices have been classified primarily by the physical state of their gain medium-solid-state (including gas and crystalline media), liquid (commonly dye lasers), gas (including ion, excimer, and gas mixture lasers), or semiconductor (most commonly made of compositions of III-V elements) and by the way the inversion level is created in their gain medium-via direct electrical current (typically in the case of gas and semiconductor gain media), via optical pumping (typically in liquid and solid-state gain media due to absorption of light from an incoherent source, such as arc lamps or flashlamps, or from a coherent source, another laser), or via a chemical reaction.

Another way lasers are classified is by temporal output, i.e., the way the light intensity is emitted from the laser in time: continuous wave, long pulse (or "free running"), Q-switched, mode-locked (or ultrafast). In continuous wave (or "cw") lasers the pumping means and the consequential light output are nominally constant, or at least continuous, in time. Typically, the output level is either on (at some fixed level) or off, with the on-level being adjustable, but usually only slowly in time. While cw lasers can be rapidly switched on and off or intensity modulated (either by modulating their gain or loss), sometimes quite rapidly according to a specific waveform (e.g., to carry an information signal), it is their generic characteristic that the peak intensity (or peak power) of the laser output is about the same level as it is when the output is on continuously; that is, the peak power of the cw laser output does not depend very much on whether or not it is being modulated.

Long pulse lasers are characterized by having a time-dependent gain that follows a time-dependent pump source, such as flashlamp output that rises and falls due to the electrical discharge through the lamp. The output of the long pulse laser has a time dependent pulse shape that turns on when the lasing condition is met (that is, when gain exceeds loss), but otherwise fairly mimics the temporal profile of the flashlamp output. Typically, these pulses have durations in the range between one microsecond and a few hundred milliseconds. Except for often unwanted, and often uncontrolled, transients (such as relaxation oscillations), both cw and long pulse lasers are characterized by an internal gain that is "clamped" at the laser threshold; that is at the point where gain equals loss.

Q-switched lasers may be pumped by either continuous or pulsed sources, but are characterized by the incorporation of a rapidly switchable dynamic loss. This is in addition to the static (or "passive") losses inherent to all lasers. During the pumping excitation, the dynamic loss is set to a level sufficiently high to frustrate the build-up of the stimulated emission. Gain builds up but does not exceed loss, so no lasing occurs. At some point, most typically when the gain achieves some predetermined value (usually proximate to the gain maximum), the dynamic loss is switched off (or to some lower level where gain exceeds loss inside the laser resonator). Stimulated emission now rapidly builds and lasing occurs until the excitation level of the gain medium falls below threshold. Because more energy can be pumped into the gain medium before lasing begins to deplete it, because the stored energy is extracted more quickly at higher net resonator gain (gain minus loss inside the laser resonator), and because, in stimulated emission, the rate of energy extraction from the gain medium increases as the light intensity inside the laser resonator increases and continues even when the gain falls below the passive loss threshold, the peak power levels achieved in a Q-switched pulse can be many orders of magnitude higher than those that could be achieved under cw or long pulse conditions.

Mode-locked lasers also may be pumped by continuous or pulsed sources and may or may not be Q-switched as well. Their defining characteristic is that the phases of the axial (or "longitudinal") modes of the laser are put into phase (typically by use of an electrooptic or acousto-optic modulator) to create a very short temporal output pulse. To make very short pulses (less than about 1 picosecond) it is also necessary to compensate for dispersion inside the laser or to create an output pulse having a specific frequency pattern that can be later compressed using dispersive (or anomalously dispersive) optical elements external to the laser producing the pulse.

Heretofore, in medicine, lasers with one of the above temporal output characteristics have been used. However, the difficulty in understanding what happens when light impinges on biological materials in general, and human tissues specifically, is that these materials are generally quite heterogeneous in character and complex in their optical, thermal, and mechanical properties and consequential biological responses.

SUMMARY OF INVENTION

In some embodiments, the instant invention includes a laser device that includes at least: a laser generating module that produces a plurality of laser pulses having a time-structured pulse format that includes at least: a plurality of micropulses, a macropulse time envelope, where the plurality of micropulses are within the macropulse time envelope; where the time-structured pulse format is configured so that the laser device is capable of treating human tissue by selectively targeting or affecting at least one first tissue or at least one first disease organisms while not substantially affecting at least one first surrounding or adjacent tissue.

In some embodiments, each of the plurality of micropulses has a duration between 1 ps and 1 ms and where the macropulse lasts between 2-1000 times longer than the duration of the micropulses.

In some embodiments, each of the plurality of micropulses has a duration between 1 and 100 ns and where the macropulse lasts between 10 and 500 microseconds.

In some embodiments, each of the plurality of micropulses has a duration between 0.1 and 1 ms and where the macropulse lasts between 3 and 300 ms.

In some embodiments, the instant invention includes a light emitting device that includes at least: a light emitting unit producing a light output having a time-structured pulse format that includes at least: a plurality of micropulses, a macropulse time envelope, where the plurality of micropulses are contained within the macropulse time envelope; where each of the plurality of micropulses has a duration between 1 and 100 ns and where the macropulse lasts between 1 and 100 microseconds; and where the time-structured pulse format is configured so that the device is capable of treating fungal nails. In some embodiments, the light emitting unit is a laser.

In some embodiments, the instant invention includes a laser device that includes at least: a laser generating module that produces a laser beam having a time-structured pulse format that includes at least: a plurality of micropulses, a macropulse time envelope, where the plurality of micropulses are contained within the macropulse time envelope; where the time-structured pulse format is configured so that the laser device is capable of removal hair by selectively targeting or affecting at least one first tissue with hair while not substantially affecting at least one first surrounding or adjacent tissue.

In some embodiments, the instant invention includes a laser that includes at least: an intracavity device to control the laser's loss during a pumping pulse, a laser generating module that produces a plurality of laser pulses having at least one specific wavelength, where the plurality of laser pulses that include at least: a sequence of laser micropulses ("pulselets"), a macropulse time envelope, where the sequence of laser pulselets is contained within the macropulse time envelope; where the laser pulselets are being limited in peak power and have pulse durations, pulse energies, and inter-pulse spacings that are configured to differentially affect human tissues, which are spatially adjacent, intermixed, or otherwise intertwined, that are capable of being differentiated based on optical, thermal, and/or mechanical properties; where each of the laser pulselets has: i) a duration between 1 ns and 10 ms, and ii) a pulse energy between 1 mJ and 1 J; and where the macropulse time envelope (i) lasts between 2 and 100 times the pulselet spacing and (ii) has a total energy equal to the sum of the pulselets' energies.

In some embodiments, the intercavity device is selected from the group of:
  i) a saturable absorber,
  ii) a pockels cell, and
  iii) a time controlled voltage modulator.

In some embodiments, the time controlled voltage modulator includes at least an intensity dependent feedback system that includes at least:
  i) a photodiode and
  ii) an electronic circuitry.

In some embodiments, the laser generating module is a pulsed excitation source.

In some embodiments, the pulse excitation source is a flashlamp or a plurality of flashlamps.

In some embodiments, a number of laser pulselets in the sequence depends on a duration of each of laser pulselets and the macropulse's energy so that the peak power of each of the laser pulselets produces an intensity less than 5 GW/cm^2 at a point on which a laser beam impinges on the human tissue.

In some embodiments, the instant invention includes a light emitting device that includes at least: a light emitting unit producing a light output having a time-structured pulse format that include at least: a plurality of micropulses, a macropulse time envelope, where the plurality of micropulses are contained within the macropulse time envelope; and where each of the plurality of micropulses, at a wavelength between 0.4 µm and 1.6 µm, has a duration shorter than 50 microseconds and a pulse energy in a range between 1 mJ and 500 mJ.

BRIEF DESCRIPTION OF THE DRAWINGS

The present invention will be further explained with reference to the attached drawings, wherein like structures are referred to by like numerals throughout the several views.

FIG. 3 shows a graph related to some embodiments of the instant invention.

Figure 1:
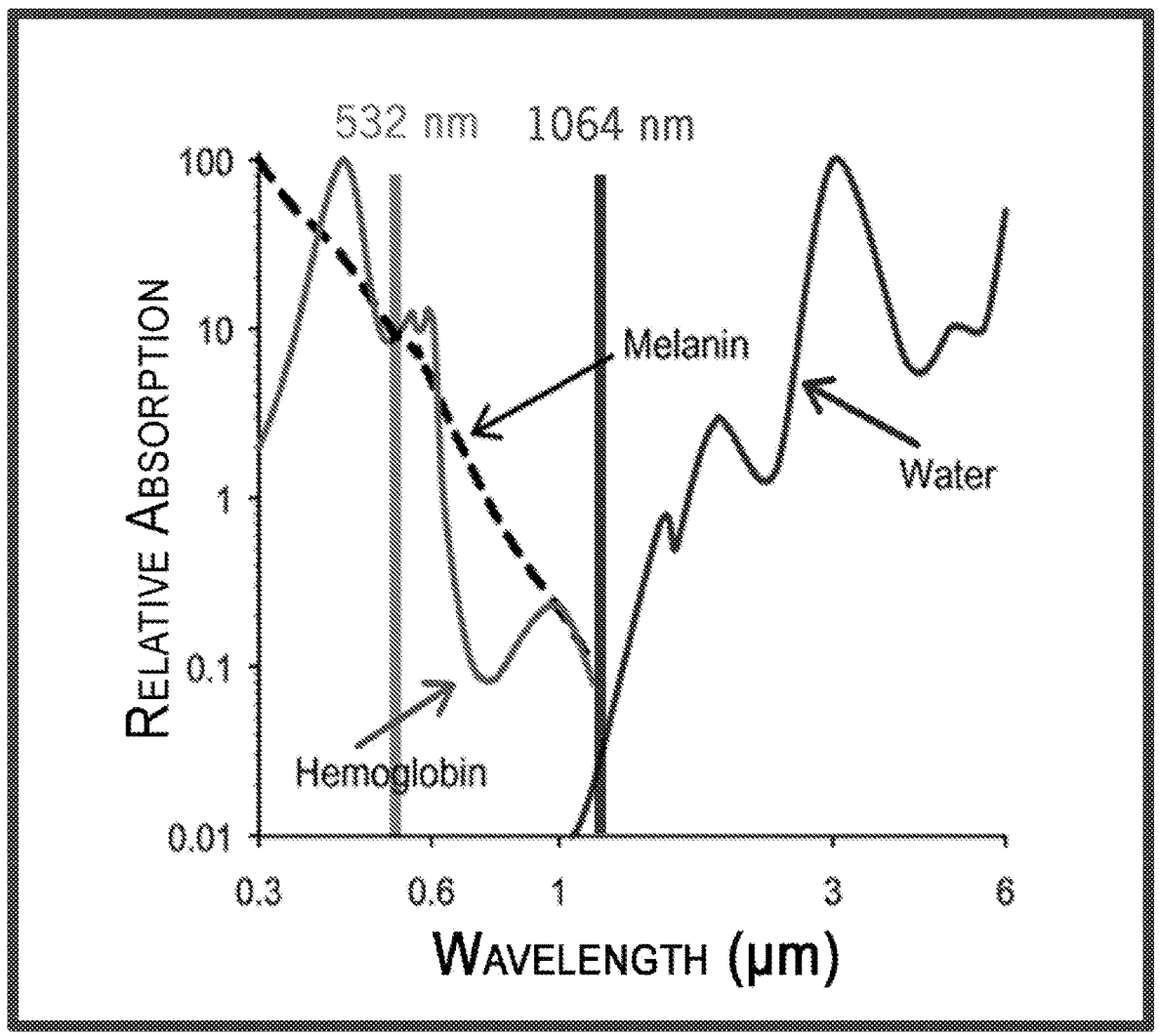
FIG. 1 shows a schematic diagram representing some embodiments of the instant invention.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive.

Throughout the specification and claims, the following terms take the meanings explicitly associated herein, unless the context clearly dictates otherwise. The phrases "In some embodiments" and "in some embodiments" as used herein do not necessarily refer to the same embodiment(s), though they may. Furthermore, the phrases "in another embodiment" and "in some other embodiments" as used herein do not necessarily refer to a different embodiment, although they may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" includes plural references. The meaning of "in" includes "in" and "on."

Some embodiments of the instant invention are directed to the medical application of lasers, similar to the medical application of drugs, based on selective interaction (or "targeting") aimed at having a specific anatomical or physiological effect. Some embodiments of the instant invention allow extending the specificity conditions beyond a wavelength—i.e., choosing not only based on the wavelength that interacts most strongly with the targeted tissue.

In some embodiments, the instant invention optimizes photothermal effects. For example, this can be accomplished by choosing wavelengths that most strongly discriminate between the targeted moiety and the surrounding tissue and by choosing a pulse duration that is sufficiently short relative to the thermal relaxation time of the target. In some embodiments, the instant invention takes into consideration at least a plurality of the following characteristics: wavelength, target relaxation times, and anti-targeting the tissue (e.g., healthy tissue) that surrounds the target. In some embodiments, to optimally anti-target the surrounding tissue, the instant invention takes into account optical, thermal, and/or mechanical properties of the anti-target tissues in addition to properties of the target. In some embodiments, the instant invention utilizes time-structured laser pulses to produce heightened differential effects on the targeted and anti-targeted tissues. In some embodiments, the instant invention generates pulses that can produce differences in photochemical, photomechanical, and/or photothermal induced biological effect in tissues or organisms that may be physically adjacent to, intercalated between, or dispersed within each other. In some embodiments, the instant invention utilizes the differences in photochemical, photomechanical, and/or photothermal induced biological effect in tissues or organisms to increase the efficacy of selectively weakening and destroying fungal structures infecting dermal tissues beneath a nail plate. In some embodiments, the same inventive principle(s) of the instant invention can be utilized to establish or enhance selective targeting of other infectious agents, while anti-targeting the surrounding tissues.

In some embodiments, the instant invention provides a laser device that produces, and a process for producing, time structured pulses (TSPs) of light having a range of properties, such as the time dependent energy profile at various wavelengths which can be used for the treatment of certain diseases and/or dystrophies. In some embodiments, in accordance with the instant invention, when light having the appropriate TSP and wavelength is focused or projected onto or into the human body by means of optical fibers, lenses, and/or other optical means, the light so impingent can selectively affect specific tissue types (for example cancerous cells), foreign pigments (such as tattoo inks or stained cells), infectious organisms (such as fungi (e.g., *Trichophyton rubrum* or bacteria), injured tissue regions, and/or dystrophic tissue regions.

For purposes of the instant disclosure, entities that are specifically intended to be materially affected by the light pulses are designated as "targets" while entities (typically tissues) that are intended not to be materially affected by the light are designated as "anti-targets."

In some embodiments, time-structured light pulses can have any functional shape. In some embodiments, the instant invention is directed to TSPs that consist of finite sequence of short duration pulses or "micropulses" (typically with durations in the range between 1 and 100 ns) contained within a time window (or "macropulse") having a duration between 100-10,000 microseconds.

In some embodiments of the instant invention, the number of micropulses and their time spacing within the macropulse can be varied to optimize their targeting and anti-targeting effects. In some embodiments, the instant invention is directed to TSPs that consist of micropulses (1) with durations in the range between 10 and 100 ns and (2) contained within a macropulse having duration between 100-1,000 microseconds. In some embodiments, the instant invention is directed to TSPs that consist of micropulses (1) with durations in the range between 50 and 100 ns and (2) contained within a macropulse having duration between 1,000-10,000 microseconds. In some embodiments, the instant invention is directed to TSPs that consist of micropulses (1) with durations in the range between 25 and 75 ns and (2) contained within a macropulse having duration between 5,000-10,000 microseconds. In some embodiments, the instant invention is directed to TSPs that consist of micropulses (1) with duration of 1 ns and (2) contained within a macropulse having duration of 1,000 microseconds. In some embodiments, the instant invention is directed to TSPs that consist of micropulses (1) with duration of 100 ns and (2) contained within a macropulse having duration of 10,000 microseconds. In some embodiments, the instant invention is directed to TSPs that consist of micropulses (1) with duration of 50 ns and (2) contained within a macropulse having duration of 5,000 microseconds.

In some embodiments, the instant invention utilizes photo-targeting that requires the impingent light to impart energy or power into the target. This causes localized heating, mechanical shock, or photochemical effects (e.g., bond breaking), or all of these effects to occur within the target. Typically, the target may contain a chromophore that absorbs light at some specific wavelength more strongly than surrounding tissue, which is desired to be anti-targeted. In some applications of the instant invention, the target may contain a higher specific absorbance than the surrounding tissue; consequently, selective targeting can be affected as a direct consequence of the primary differential light absorption and the localized response (heating, shock or photochemistry) that results. In some embodiments of the instant invention, the nature and magnitude of the response subsequent to the primary photoabsorption can depend on a number of properties and/or characteristics that are intrinsic and/or extrinsic to the target. In some embodiments of the instant invention, these intrinsic and/or extrinsic properties and/or characteristics can include, inter alia: the target's:
 heat capacity,
 thermal conductivity,
 stress-strain moduli,
 coupling to its environment due to, for example, the density and/or nature of the surrounding tissue, and/or density of vascular support and blood flow.

In some embodiments of the instant invention, utilizes selective photothermolysis which is a condition where selective destruction of the target is caused by selective primary photoabsorption of light at some wavelength followed by the degradation of the energy absorbed into heat resulting in a localized temperature rise within the target which is confined within the target for a timescale long enough to kill the target. In some embodiments, the instant invention anti-targets tissue based on a premise that properties of healthy tissues are similar to encapsulated water, which makes up roughly 80-90% of tissue mass.

In some embodiments, the instant invention targets fungal tissues while anti-targeting dermal tissue. by modulating the time-structured pulse format. In some embodiments, the instant invention selects at least:

(1) the duration of the micropulses to be much shorter that the thermal relaxation time of the fungal (hyphae) targets and (2) the spacing between micropulses within the macropulse envelope to be sufficient to permit temperature buildup within the hyphae fungal units during the pulse.

In some embodiments, based on the above selection, the adjacent dermal tissues, having higher heat capacity and better thermal conductivity as well as being better coupled to the vascular structure into which some of the heat is eventually dissipated, is anti-targeted by selecting a time spacing between micropulses that is long enough so that the dermal cells remain viable (e.g., their internal temperature remains below approximately 45° C.).

As described above for at least some embodiments, the selection of a wavelength where more light energy is deposited into the fungus than into the adjacent dermal tissues is taken into consideration. In some embodiments, providing sufficient peak power (micropulse energy in a short enough period of time) to provide a mechanical shock into the fungus to increase the selective photolethality. In some embodiments, the instant invention utilizes micropulses of energies between 50 and 500 mJ in durations of 1 to 10 ns to selectively clear nails from fungal infections when the wavelength used is 1064 nm and the macropulse envelope contains 1~4 micropulses spaced 10-30 us apart with the spot size incident on the nail plate is 1-3 mm in diameter. In some embodiments, the instant invention utilizes micropulses of energies between 100 and 500 mJ in durations of 5 to 10 ns to selectively clear nails from fungal infections when the wavelength used is 1064 nm and the macropulse envelope contains 2-4 micropulses spaced 20-30 us apart with the spot size incident on the nail plate is 1-3 mm in diameter. In some embodiments, the instant invention utilizes micropulses of energies between 250 and 500 mJ in durations of 7 to 10 ns to selectively clear nails from fungal infections when the wavelength used is 1064 nm and the macropulse envelope contains 3-4 micropulses spaced 20-30 us apart with the spot size incident on the nail plate is 1-3 mm in diameter. In some embodiments, the instant invention utilizes micropulses of energies between 50 mJ in durations of 10 ns to selectively clear nails from fungal infections when the wavelength used is 1064 nm and the macropulse envelope contains 4 micropulses spaced 10 us apart with the spot size incident on the nail plate is 1-3 mm in diameter. In some embodiments, the instant invention utilizes micropulses of energies between 100 and 500 mJ in durations of 1-10 ns to selectively clear nails from fungal infections when the wavelength used is 1064 nm and the macropulse envelope contains 2-4 micropulses spaced 10-30 us apart with the spot size incident on the nail plate is 1-3 mm in diameter.

In some embodiments, the selective photlethality can be obtained when the instant invention utilizes wavelengths between 500 nm and 1500 nm. In some embodiments, the selective photlethality can be obtained when the instant invention utilizes wavelengths in a range between 700-1100 nm which are not, typically, strongly absorbed by the dermal tissues and can penetrate even most moderately dystrophic nail plates. In some embodiments, the selective photlethality can be obtained when the instant invention utilizes wavelength of 500 nm. In some embodiments, the selective photlethality can be obtained when the instant invention utilizes wavelength of 750 nm. In some embodiments, the selective photlethality can be obtained when the instant invention utilizes wavelength of 1000 nm.

In some embodiments, perceived pain can is also less at wavelengths in the range between 700-1100 nm which have been found to penetrate deeply through dermal tissues. In some embodiments, wavelengths longer than 750 nm (and proximate to 1064 nm) have been shown to be less painful for patients with darker skin types (e.g., Fitzpatrick V and VI), as these wavelengths are less strongly absorbed by melanin in the skin. In some embodiments, the instant invention utilizes wavelengths sufficiently short enough so that water absorption is less, because dermal tissues generally contain more water per unit volume than do fungal cells.

While 1064 nm is a wavelength that is only weakly absorbed both by melanin and water putting i=t in a preferred wavelength region, it is advantaged because it is the fundamental output of Nd: YAG lasers, one of the most widely and inexpensively produced solid-state laser systems.

In some embodiments, the instant invention utilizes a Q-switched Nd: YAG systems where the switching is caused by electrooptic means such as a pockels cell and polarizer or an electrooptic or acoustooptic modulator. In some embodiments, the instant invention utilizes Q-switching that may be accomplished by using a saturable absorber such as and the peak power of the system is limited by setting the concentration of the saturable absorber and the size of the beam impingent upon it.

FIG. 1 shows the exemplary absorption spectrum, in the visible and near infrared, of various skin components [Melanin, Hb, HbO, water] and their relationship to the Nd: YAG laser fundamental and second harmonic wavelengths as utilized in some embodiments of the instant invention. In some embodiments, the instant invention utilizes absorption spectra that provide the absorption cross sections for various targeted and anti-targeted materials to select operational wavelengths for visible and near IR lasers to be employed in accordance with the invention. In some embodiments, the instant invention utilizes absorption of the laser light as the basis for initial differential deposition of energy and subsequent, consequential photomechanical, photochemical, and photothermal interaction. In some embodiments, for photothermal targeting and anti-targeting, the instant invention can further utilize the subsequent differential effect on the internal temperatures of the target and the anti-target. Those effects are given by the following differential equations (1)-(2) governing the consequential effects on those temperatures for the target $T^T$ (t) and anti-target $T^{aT}$ (t), respectively.

$$C_V^T \frac{dT^T(x,t)}{dt} = \sigma^T(\lambda) I(\lambda; x, t) + \qquad (1)$$
$$\alpha_{T \leftrightarrow aT}[T^{aT}(x,t) - T^t(x,t)] - \alpha_{T \leftrightarrow amb}[T^T(x,t) - T^{amb}(x,t)]$$

$$C_V^{aT} \frac{dT^{aT}(x,t)}{dt} = \sigma^{aT}(\lambda) I(\lambda; x, t) + \qquad (2)$$
$$\alpha_{T \leftrightarrow aT}[T^T(x,t) - T^{aT}(x,t)] - \alpha_{aT \leftrightarrow amb}[T^{aT}(x,t) - T^{amb}(x,t)]$$

where σ denotes the absorption cross section for Target (T) and antiTarget (aT), respectively and a denotes the thermal exchange rate constants between Target and anti-Target and between either and the ambient (e.g., body) temperature to which they relax. Cv is the corresponding (volumetric) heat capacity.

Figure 2:
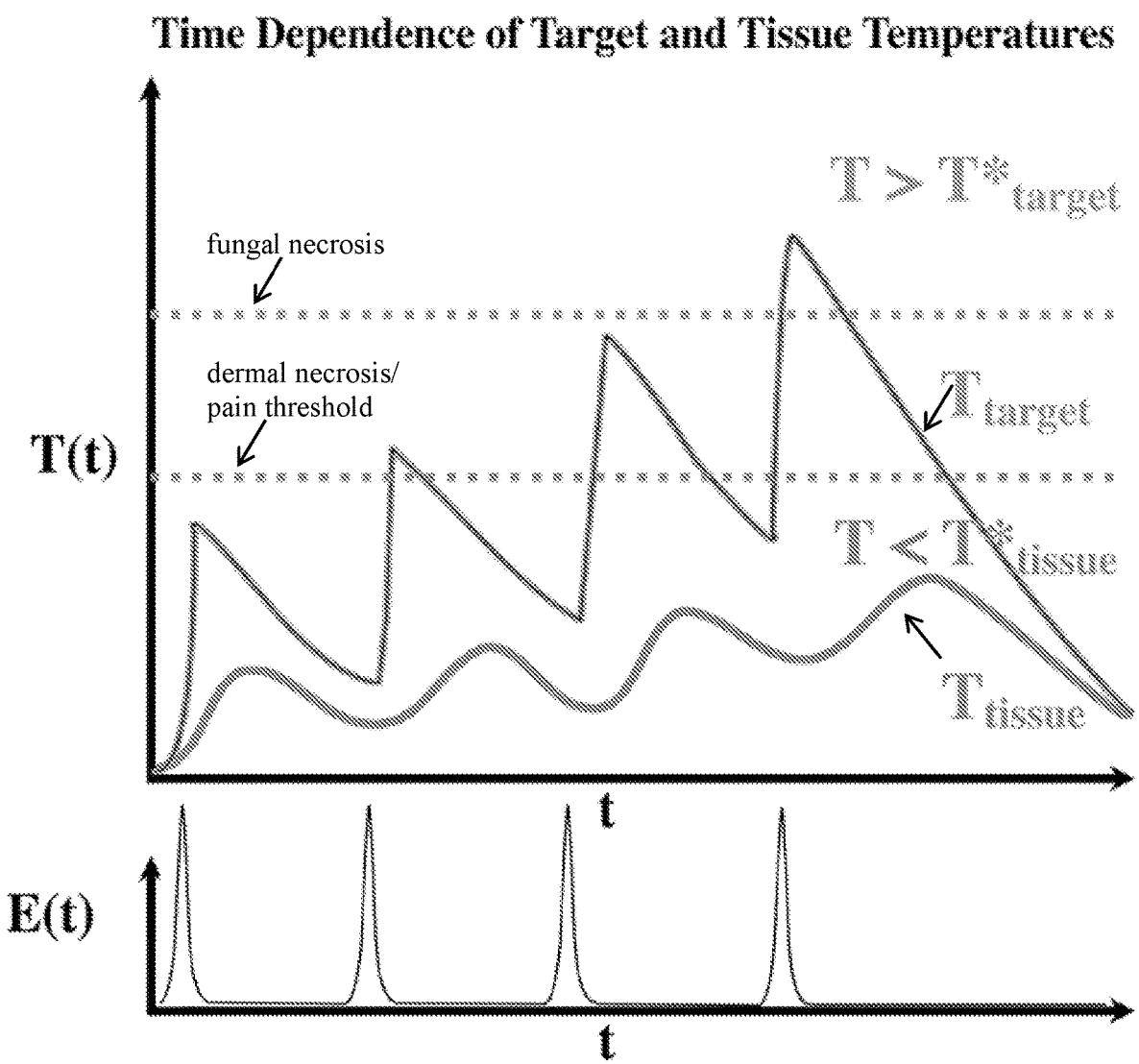
FIG. 2 shows a graph related to some embodiments of the instant invention.

A schematic example of the time dependent temperatures of the Target and anti-Target following the absorption of an impingent time-structured laser pulse, in accordance with some embodiments of the instant invention, can be seen in FIG. 2. FIG. 2. illustrates solutions to the above equations for specific choices of target and anti-target characteristics heat transfer and thermodynamic characteristics. In some embodiments of the instant invention, the difference in temperatures depends on the differences in absorption cross section as well as differences in their heat capacities, thermal conductivities and couplings between the target and anti-target and to their (ambient) environment (thermal relaxation rates).

In some embodiments, the same exemplary but not limiting, factors of the differences in absorption cross section as well as differences in their heat capacities, thermal conductivities and couplings between the target and anti-target and to their (ambient) environment (thermal relaxation rates) that govern the selection of sufficient micropulse energy and pulse duration, micropulse spacing, and macropulse duration and macropulse total energy and repetition rate.

In some embodiments of the instant invention, the inventive pulse structure is utilized to provide differential effect in response between target and anti-target. In some embodiments, when there may not be a large difference in linear absorbance and nonlinear susceptibilities between target and anti-target, the instant invention exploits the differential photothermal effects to achieve the desired remedial result(s). FIG. 2 gives an illustration of how some embodiments of the instant invention can exploit the differential photothermal effects to achieve the desired remedial result(s). In some embodiments, the instant invention utilizes clinical studies to determine whether the differential photothermal effects achieve the desired remedial result(s).

In some embodiments, the instant invention utilizes time-structured pulses that have a peak power limit—the highest peak power that can be delivered to the target must remain below that which can harm the anti-targeted tissue. In some embodiments of the instant invention, based on the peak power limit, the time-structured pulses are sufficiently designed to impart the largest temperature rise in the target consistent with maintaining the temperature rise in the anti-targeted tissues below that which is harmful to them. In some embodiments, to achieve the sufficient remedial effect, the temperature rise in the target must exceed and remain above some critical temperature (T*) for a period long enough to sufficiently damage the target. In some embodiments, where the target is an infectious organism, the induced temperature rise must be sufficient to kill it or weaken to such a degree that the body defenses can deal with it more effectively. In some embodiments, the instant invention allows to treat with fungal infections under the nail plate, where laser wavelengths are constrained to those that can penetrate the nail plate, even when the nail plate may be somewhat dystrophic. In some embodiments, the instant invention allows to treat severe cases of dystrophy and avoid the need for nail plate avulsion.

In some embodiment, the optimization of the instant invention is based at least in part on the following criteria:
i) Laser Wavelength;
ii) Laser Temporal Characteristics;
iii) Laser Fluences; and
iv) Defining Optimal Treatment Protocols.

Illustrative Example 1 Related to Some Embodiments of the Instant Invention

In some embodiments, the instant invention uses the inventive time-structured pulses for the selective photolysis of fungi infecting human dermal tissues under the nail plate of toes or fingers (Onychomycosis). For example, the fungal target and its environment are thermally coupled. The time rate of temperature (T) at any point (x) is proportional to the heat (Q) flowing into any infinitesimal volume about x at time (t):

$\partial_t T(x,t) = k(x) Q(x,t)$, where k is the inverse specific heat.

For an anisotropic medium this becomes:

$\partial_t T(x,t) = k(x) \, S_{ij} \partial xi \, (a_{ij}(x) \, \partial xjT \, (x,t))$, where $a_{ij}$ is the (anisotropic) thermal conductivity.

For an initial deposition of heat into a nearly isotropic medium at point x=s, solutions are of the form:

$T(x-s,t) = [1/8 \, (\pi k t)^{3/2}] \exp [(x-s)^2/4kt]$, where k is the thermal diffusivity [k=a/Cv, with a being the thermal conductivity (W/(m-°K) and Cv being the volumetric heat capacity=pCp (J/m³-°K)].

For a boundary cooled spherical object, so heated, the timescale over which the temperature relaxes back to the ambient value is $tr \approx d^2/16k$.

For Dermatophytes this is about 2 μs; for dermal cells, it is significantly shorter. For example, the thermal relaxation time of fungal hyphae can be at least three times longer than the thermal relaxation time of dermal cells. Moreover, dermal cells can typically have higher heat capacity, owing largely to their higher internal hydration levels, and higher thermal conductivity, dermal cells are enclosed by a permeable cell membrane rather than a chitinous cell wall. Further, dermal tissues are, typically, relatively well-vascularized, providing additional means for heat dissipation, while the fungal mycelia are not. As a consequence, by using the inventive time-structured pulse sequence, where the duration of each micro pulse is much shorter than the thermal relaxation time of the fungal target, but with spacing that permits some thermal relaxation of the nearby dermal tissues, selective thermal stress can be imparted to the fungal target even though their thermal tolerance (up to 65° C.) is higher than the dermal cells (below 45° C.) and even when the relative absorption cross sections do not substantially favor initial light-energy deposition in the fungi (an assumed condition for the standard theory of selective photothermolysis).

In accordance with a clinical study of dystrophic nails, having a clinical diagnosis of onychomycosis, using the inventive time-structured pulses from an Nd: YAG laser (having output wavelength of 1064 nm in its fundamental), significant improvement occurred in 97% of the 100 cases treated. The exemplary time-structured pulses used in the study were characterized by the following: micropulse energy ≈100-200 mJ, micropulse duration 3-7 ns, spacing between micropulses 20-30 microseconds, number of micropulses=2-5, pulse fluence (4-14 J/cm², with optimum range, for maximum effectiveness with minimal adverse side effect, ≈6-12 J/cm²). In the treatment the macropulse rate was selected to be between 1 and [−]] 5 pulses per second, the latter pulse rate chosen for treatment speed and convenience. The pulses were scanned across the nail plate so that multiple successive macropulses did not impinge ("dwell") on the same treatment spot; consequently, the selected rate is not limiting as to other rates that could have been employed in accordance with the instant invention.

In some embodiments of the instant invention, dwelling could improve efficacy, but may result in increased pain and other unwanted adverse side-effects. In some embodiments, the instant invention can use lower energy micropulses by requiring more micropulses to be used in the macropulse, while lower macropulse energy requires "dwelling" to maintain efficacy. In some embodiments of the instant invention, at least some efficacy has been achieved using the second harmonic Nd:YAG wavelength of 532 nm using the inventive time-structured pulses.

Referring to FIG. 3, which illustrates results of a retrospective study of N=100 patients that were randomly selected from more than 400 treated cases: the subjects were blind graded for nail plate clearance. The subjects ranged from 3-12 months post treatment (Tx). Significant improvement was observed in more than 97% of subjects. 0% subjects identified the presence of pain and 0% subjects identified adverse side effects. Average Clearance of 57% across all subjects and over 20% of the complete clearance were observed across all subjects. As FIG. 3 illustrates that essentially all fungi were killed in a single treatment.

Illustrative Example 2 Related to Some Embodiments of the Instant Invention

In some embodiments, the instant invention utilizes the inventive time-structured pulses for selectively targeting hair growing in dermal tissues, by, for example, using either 1064 nm or 755 nm wavelengths and micropulses having durations between 0.5 and 5 ms that are evenly spaced within a macropulse having a duration between 10 and 300 ms. In some embodiments, for selectively targeting hair growing in dermal tissues, sufficiently effective macropulse energies ranged between 5 and 70 J and macropulse fluences were between 8 and 50 J/cm2.

Some Other Illustrative Examples Related to Some Embodiments of the Instant Invention In some embodiments, the instant invention includes a laser device that includes at least: a laser pulse generating module that produces a plurality of laser pulses having a time-structured pulse format that includes at least: a plurality of micropulses, a macropulse time envelope, where the plurality of micropulses are within the macropulse time envelope; where the time-structured pulse format is configured so that the laser device is capable of treating human tissue by selectively targeting or affecting at least one first tissue or at least one first disease organisms while not substantially affecting at least one first surrounding or adjacent tissue.

In some embodiments, each of the plurality of micropulses has a duration between 1 ps and 1 ms and where the macropulse lasts between 2-1000 times longer than a total duration of the plurality of micropulses.

In some embodiments, each of the plurality of micropulses has a duration between 1 and 100 ns and where the macropulse lasts between 10 and 500 microseconds.

In some embodiments, each of the plurality of micropulses has a duration between 0.1 and 1 ms and where the macropulse lasts between 3 and 300 ms.

In some embodiments, the instant invention includes a light emitting device that includes at least: a light emitting unit producing a light output having a time-structured pulse format that includes at least: a plurality of micropulses, a macropulse time envelope, where the plurality of micropulses are contained within the macropulse time envelope; where each of the plurality of micropulses has a duration between 1 and 100 ns and where the macropulse lasts between 1 and 100 microseconds; and where the time-structured pulse format is configured so that the device is capable of treating fungal nails. In some embodiments, the light emitting unit is a laser.

In some embodiments, the instant invention includes a laser device that includes at least: a laser generating module that produces a laser beam having a time-structured pulse format that includes at least: a plurality of micropulses, a macropulse time envelope, where the plurality of micropulses are contained within the macropulse time envelope; where the time-structured pulse format is configured so that the laser device is capable of removal hair by selectively targeting or affecting at least one first tissue with hair while not substantially affecting at least one first surrounding or adjacent tissue.

In some embodiments, the instant invention includes a laser that includes at least: an intracavity device to control the laser's loss during excitation (e.g., optical pumping) of its gain material, a laser generating module that produces a plurality of laser pulses having at least one specific wavelength, where the plurality of laser pulses that include at least: a sequence of laser pulselets, a macropulse time envelope, where the sequence of laser pulselets is contained within the macropulse time envelope; where the laser pulselets are being limited in peak power and have pulse durations, pulse energies, and inter-pulse spacings that are configured to differentially affect human tissues, which are spatially adjacent, intermixed, or otherwise intertwined, that are capable of being differentiated based on optical, thermal, and/or mechanical properties; where each of the laser pulselets has: i) a duration between 1 ns and 10 ms, and ii) a pulse energy between 1 mJ and 1 J; and where the macropulse time envelope (i) lasts between 2 and 100 times the pulselet spacing and (ii) has a total energy equal to the sum of the pulselets' energies.

In some embodiments, the intercavity device is selected from the group of:
   i) a saturable absorber,
   ii) a pockels cell, and
   iii) a time controlled voltage modulator.

In some embodiments, the time controlled voltage modulator includes at least an intensity dependent feedback system that includes at least:
   i) a photodiode and
   ii) an electronic circuitry.

In some embodiments, the laser generating module is a pulsed excitation source.

In some embodiments, the pulse excitation source is a flashlamp or a plurality of flashlamps.

In some embodiments, a number of laser pulselets in the sequence depends on a duration of each of laser pulselets and the macropulse's energy so that the peak power of each of the laser pulselets produces an intensity less than 5 GW/cm^2 at a point on which a laser beam impinges on the human tissue.

In some embodiments, the instant invention includes a light emitting device that includes at least: a light emitting unit producing a light output having a time-structured pulse format that includes at least: a plurality of micropulses, a macropulse time envelope, where the plurality of micropulses are contained within the macropulse time envelope; and where each of the plurality of micropulses, at a wavelength between 0.4 µm and 1.6 µm, has a duration shorter than 50 microseconds and a pulse energy in a range between 1 and 500 mJ.

In some embodiments, the inventive principles and devices of the instant invention can be utilize to perform at least one of the following:

Incision, Excision, Ablation, and Vaporization of Soft Tissue for General Dermatology;
Tattoo Rremoval: Dark and Light Inks;
Treatment of Pigmented Lesions;
Treatment of Vascular Lesions;
Treatment of Café-au-lait Spots;
Treatment of Seborrheic Keratoses; and
Skin Resurfacing.

While a number of embodiments of the present invention have been described, it is understood that these embodiments are illustrative only, and not restrictive, and that many modifications may become apparent to those of ordinary skill in the art. Further, any steps described herein may be carried out in any desired order (and any steps may be added and/or deleted).

What is claimed is:

1. A method comprising:
    impinging upon a volume of human tissue with at least one Time-Structured laser Pulse (TSP) of a laser beam;
        wherein the volume of human tissue is defined by an incident spot size of the laser beam and a penetration depth defined by absorption and scattering characteristics of the human tissue at a wavelength of the TSP;
        wherein the volume of human tissue comprises a targeted moiety and a portion of human tissue to be spared from a thermal damage;
        wherein the targeted moiety comprises a fungal pathogen known to cause onychomycosis, which is embedded in, surrounded by, or adjacent to the portion of human tissue that is to be spared from the thermal damage;
        wherein the TSP
        i) is characterized by at least one wavelength that is more strongly absorbed by the targeted moiety and less strongly absorbed by the portion of the human tissue to be spared from the thermal damage, and
        ii) comprises: a plurality of short duration components ("micropulses") within a time envelope ("macropulse");
            wherein the TSP comprises one or more wavelengths between 0.4 μm and 1.6 μm,
            wherein a duration of each of the plurality of micropulses is 3 ns to 7 ns,
            wherein each micropulse has an energy of 100 mJ to 200 mJ,
            wherein the micropulses have temporal spacings such that 2 to 5 micropulses exist within a macropulse duration,
            wherein the macropulse duration is 40 us to 150 μs,
            wherein an energy per unit area of the laser beam 4 J/cm2 to 14 J/cm2 for any macropulse,
            wherein the plurality of micropulses each has a pulse durations that is shorter in time than a thermal relaxation time of the targeted moiety and spaced in time by intervals that are
            a) long enough so as to permit a thermal relaxation of the portion of the human tissue to be spared from the thermal damage to limit the thermal damage of the portion of the human tissue and
            b) short enough so as to provide a temperature increase within the targeted moiety so as to cause the thermal damage to the targeted moiety.

2. The method of claim 1, further comprising:
    utilizing a laser device to produce the TSP;
        wherein the laser device comprises a q-switched Nd: YAG laser.

3. The method of claim 1, further comprising: utilizing a laser device to produce the TSP;
    wherein the laser device is a long pulse ("normal mode") laser having a wavelength of 755±50 nm or a long pulse ("normal mode") laser having a wavelength of 1064 nm Nd: YAG laser.

4. The method of claim 1, wherein the wavelength and characteristics of the plurality of micropulses within the macropulse are determined based on:
    a spectral absorption of the TSP by the targeted moiety;
    a spectral absorption of the TSP by the portion of human tissue to be spared from the thermal damage;
    a thermal exchange rate of the targeted moiety and the portion of human tissue to be spared from the thermal damage when applying the TSP;
    a heat capacity and thermal conductivity of the targeted moiety; and
    a heat capacity and thermal conductivity of the portion of human tissue to be spared from the thermal damage.

5. A system, comprising:
    a laser, wherein the laser is configured to:
    impinge upon a volume of human tissue with at least one Time-Structured laser Pulse (TSP) of a laser beam;
        wherein the volume of human tissue is defined by an incident spot size of the laser beam and a penetration depth defined by absorption and scattering characteristics of the human tissue at a wavelength of the TSP;
        wherein the volume of human tissue comprises a targeted moiety and a portion of human tissue to be spared from a thermal damage;
        wherein the targeted moiety comprises a fungal pathogen known to cause onychomycosis, which is embedded in, surrounded by, or adjacent to the portion of human tissue that is to be spared from the thermal damage;
        wherein the TSP
        i) is characterized by at least one wavelength that is more strongly absorbed by the targeted moiety and less strongly absorbed by the portion of the human tissue to be spared from the thermal damage, and
        ii) comprises: a plurality of short duration components ("micropulses") within a time envelope ("macropulse");
            wherein the TSP comprises one or more wavelengths between
            wherein a duration of each of the plurality of micropulses is 3 ns to 7 ns,
            wherein each micropulse has an energy of 100 mJ to 200 mJ,
            wherein the micropulses have temporal spacings such that 2 to 5 micropulses exist within a macropulse duration,
            wherein the macropulse duration is 40 us to 150 μs,
            wherein an energy per unit area of the laser beam is 4 J/cm2 to 14 J/cm2 for any macropulse,
            wherein the plurality of micropulses each has a pulse durations that is shorter in time than a thermal relaxation time of the targeted moiety and spaced in time by intervals that are
            a) long enough so as to permit a thermal relaxation of the portion of the human tissue to be spared from the thermal damage to limit the thermal damage of the portion of the human tissue and b) short enough so as to provide a temperature increase within the targeted moiety so as to cause the thermal damage to targeted moiety.

6. The system of claim 5, wherein the laser is a q-switched Nd: YAG laser.

7. The system of claim 5, wherein the laser is a long pulse ("normal mode") laser having a wavelength of 755±50 nm or a long pulse ("normal mode") laser having a wavelength of 1064 nm Nd: YAG laser.

8. The system of claim 5, wherein the wavelength and characteristics of the plurality of micropulses within the macropulse are determined based on:

a spectral absorption of the TSP by the targeted moiety;

a spectral absorption of the TSP by the portion of human tissue to be spared from the thermal damage;

a thermal exchange rate of the targeted moiety and the portion of human tissue to be spared from the thermal damage when applying the TSP;

a heat capacity and thermal conductivity of the targeted moiety; and a heat capacity and thermal conductivity of the portion of human tissue to be spared from the thermal damage.

* * * * *